US012496261B2

(12) United States Patent
Chen et al.

(10) Patent No.: US 12,496,261 B2
(45) Date of Patent: Dec. 16, 2025

(54) METHOD OF INCREASING THE FOAMING PROPERTIES OF DETERGENT COMPOSITIONS BY USE OF SACCHARIDE ISOMERATE

(71) Applicant: DSM IP Assets B.V., Heerlen (NL)

(72) Inventors: Linjing Chen, Kaiseraugst (CH); Guillaume Bernard Laurent, Kaiseraugst (CH); Pascal Christian Sieber, Kaiseraugst (CH); Xiangxiang Zhang, Kaiseraugst (CH)

(73) Assignee: DSM IP ASSETS B.V., Maastricht (NL)

( * ) Notice: Subject to any disclaimer, the term of this patent is extended or adjusted under 35 U.S.C. 154(b) by 506 days.

(21) Appl. No.: 17/799,972

(22) PCT Filed: Feb. 16, 2021

(86) PCT No.: PCT/EP2021/053722

§ 371 (c)(1),
(2) Date: Aug. 16, 2022

(87) PCT Pub. No.: WO2021/165232

PCT Pub. Date: Aug. 26, 2021

(65) Prior Publication Data

US 2023/0080506 A1 Mar. 16, 2023

(30) Foreign Application Priority Data

Feb. 18, 2020 (EP) .................................... 20157954

(51) Int. Cl.

| | |
|---|---|
| ***A61K 8/04*** | (2006.01) |
| ***A61K 8/34*** | (2006.01) |
| ***A61K 8/36*** | (2006.01) |
| ***A61K 8/60*** | (2006.01) |
| ***A61Q 19/10*** | (2006.01) |

(52) U.S. Cl.

CPC .............. *A61K 8/046* (2013.01); *A61K 8/345* (2013.01); *A61K 8/361* (2013.01); *A61K 8/60* (2013.01); *A61Q 19/10* (2013.01)

(58) Field of Classification Search

CPC ....... C11D 3/221; C11D 3/0094; C11D 3/046; C11D 1/662; C11D 3/3707; C11D 1/146; C11D 1/29; C11D 3/222; C11D 1/37; C11D 1/90; C11D 1/94; C11D 3/0073; C11D 3/044; C11D 3/2058; C11D 3/2072; C11D 3/2093; C11D 3/349; C11D 3/3765; C11D 3/50; C11D 3/373; C11D 3/3757; C11D 17/041; C11D 3/0015; C11D 3/162; C11D 3/362; C11D 3/3738; C11D 3/3769; C11D 1/667; C11D 1/825; C11D 10/04; C11D 17/006; C11D 17/047; C11D 3/225; C11D 3/3753; C11D 3/3776; C11D 9/262; C11D 1/12; C11D 1/143; C11D 1/72; C11D 1/83

See application file for complete search history.

(56) References Cited

U.S. PATENT DOCUMENTS 4,364,837 A 12/1982 Pader

FOREIGN PATENT DOCUMENTS

| | | | |
|---|---|---|---|
| CN | 106535869 | 3/2017 | |
| CN | 108884418 | 11/2018 | |
| EP | 0 545 716 | 6/1993 | |
| EP | 0545716 A1 * | 6/1993 | ............ C11D 17/00 |
| EP | 1 661 976 | 5/2006 | |
| JP | H04-170499 | 6/1992 | |
| JP | H05-320700 | 12/1993 | |
| JP | 2007-508403 | 4/2007 | |
| JP | 2010-285392 | 12/2010 | |
| JP | 2019-506453 | 3/2019 | |
| WO | 99/55303 | 11/1999 | |
| WO | 2008/003779 | 1/2008 | |
| WO | 2016/066812 | 5/2016 | |
| WO | 2017/137905 | 8/2017 | |
| WO | WO2017137905 A1 * | 8/2017 | ............... C11D 3/22 |
| WO | WO 2019/170502 | 9/2019 | |

OTHER PUBLICATIONS

"Product Information, Product Data Sheet, Pentavitin" Jul. 10, 2015. DSM Nutritional Products (3 pages).
"Pentavitin, Binds to Keratin in Skin to Keep the Moisture Balance" Jan. 1, 2009. DSM Nutritional Products (2 pages).
International Search Report and Written Opinion of the ISA for PCT/EP2021/053722, dated Apr. 21, 2021 (16 pages).

* cited by examiner

*Primary Examiner* — Audrea B Coniglio
(74) *Attorney, Agent, or Firm* — NIXON & VANDERHYE P.C.

(57) ABSTRACT

The present invention relates to a method of increasing the foaming properties of detergent compositions comprising at least one surfactant by incorporation of saccharide isomerate.

22 Claims, No Drawings

METHOD OF INCREASING THE FOAMING PROPERTIES OF DETERGENT COMPOSITIONS BY USE OF SACCHARIDE ISOMERATE

This application is the U.S. national phase of International Application No. PCT/EP2021/053722 filed Feb. 16, 2021 which designated the U.S. and claims priority to EP 20157954.7 filed Feb. 18, 2020, the entire contents of each of which are hereby incorporated by reference.

The present invention relates to a method of increasing the foaming properties of detergent compositions comprising at least one surfactant by incorporation of saccharide isomerate into said detergent composition.

In a number of detergent applications, consumers are looking for a high foaming capacity. For example, a shampoo that does not produce enough creamy, stable foam during shampooing has no chance of success on the market. The same applies to manual dishwashing detergents, even though a direct connection between the foaming capacity and the cleaning performance cannot be established at all in many cases.

Hence, besides performance requirements, such as cleaning performance and dermatological compatibility, the foaming behavior is a further important product feature. However, not all surfactant mixtures which perform satisfactorily and are economical in use show the required foaming behavior.

Thus, there is an ongoing need of ingredients which are able to increase the foaming properties of a detergent composition without compromising the cleansing properties thereof.

Surprisingly it has been found that saccharide isomerate significantly increases the foaming characteristics of detergent compositions.

Thus, in a first aspect, the present invention relates to a method of increasing the foaming properties of a detergent composition comprising at least one surfactant, said method comprising the step of adding saccharide isomerate into said cleansing composition and optionally appreciating the effect.

In a second aspect, the present invention relates to the use of saccharide isomerate as foam-enhancing agent or foam booster, in particular in detergent compositions comprising at least one surfactant selected from the group consisting of anionic, cationic, non-ionic and amphoteric surfactants.

In a further embodiment, the present invention relates to a method for improving the foaming properties of anionic, cationic, non-ionic and/or amphoteric surfactants or mixtures thereof in a detergent composition, which method comprises combining saccharide isomerate with the at least one surfactant.

The term 'foam-enhancing agent' as used herein refers to an agent which favorably influences the foam properties of a detergent composition with regard to foaming ability, foam stability (foam remaining after certain period at rest), foam quantity/volume (associated with good cleaning effect), creaminess of the foam (associated with conditioning effect), foam density, texture of the foam and/or foam speed (foam produced after a very short period of time.

Saccharide isomerate (CAS 100843-69-4) is a well-known cosmetic agent with unique binding mechanism to the skin used for short and long-lasting moisturization.

The most preferred saccharide isomerate in all embodiments of the present invention is a saccharide isomerate consisting essentially of a) 1.5 to 5 wt.-%, preferably 2 to 4 wt.-%, of psicose, b) 1 to 5 wt.-%, preferably 1.5 to 4.5 wt.-%, of mannose, c) 10 to 30 wt.-%, preferably 15 to 30 wt.-%, of fructose, d) 20 to 60 wt.-%, preferably 25 to 60 wt.-%, of glucose, and e) 0 to 5 wt.-%, preferably 0 to 4 wt.-%, of galactose.

The term 'consisting essentially of' as used herein means that specific further components can be present, namely those not materially affecting the essential characteristics of the compound or composition. Ideally the total amount of the listed ingredients sum up to 100 wt.-%. It is however not excluded that small amount of unknown (sugar) impurities derived from the isomerisation process may be present, however only in amounts of up to 5 wt.-%, preferably up to 2.5 wt.-%, most preferably up to 1.5 wt.-%.

Most preferably, in all embodiments of the present invention, the saccharide isomerate consists essentially of a) 2 to 3 wt.-% of psicose, b) 1.5 to 2.5 wt.-% of mannose, c) 15 to 25 wt.-% of fructose, d) 20 to 40 wt.-% of glucose and e) 0 to 1 wt.-% of galactose.

Said saccharide isomerate consisting essentially of the ingredients a) to e) is prepared by isomerisation of plant derived glucose and commercially available as an aqueous solution thereof (25-50 wt.-%) under the tradename PENTAVITIN® from DSM Nutritional products Ltd. Said saccharide isomerate has also been used in the examples.

The amount of the saccharide isomerate used according to the present invention is preferably selected in the range from 0.01 to 10 wt.-%, more preferably in the range from 0.1 to 7.5 wt.-%, most preferably in the range from 0.2 to 5 wt.-%, based on the total weight of the detergent composition. Further suitable ranges are from 0.25 to 2.5 wt.-% and from 0.5 to 2 wt.-%. Particularly preferred ranges according to the present invention are from 0.2 to 1 wt.-%, more preferably from 0.25 to 0.75 wt.-%, such as from 0.3 to 0.6 wt.-%.

In one advantageous embodiment, the detergent compositions according to the present invention preferably comprises at least one anionic and/or at least one zwitterionic surfactant such as in particular a laureth sulfate and/or an alkyl amidopropyl betaine, most in particular said detergent comprise as surfactant at least sodium laureth sulfate and/or cocamidopropyl betaine, even more preferably in the absence of a soap. The total amount of such anionic and/or zwitterionic surfactants is in said detergent compositions is preferably selected in the range from 30 to 75 wt.-%, most preferably in the range of 40 to 60 wt.-%. Most preferably said detergent compositions furthermore comprise at least at least 40 wt.-% of water, most preferably at least 45 wt.-% of water, based on the total weight of said detergent compositions.

In another particular advantageous embodiment, the at least one surfactant present in the detergent compositions according to the present invention preferably comprises at least one soap.

The term "soap" is used herein in its popular sense, i.e., it refers to the alkali metal or alkanol ammonium salts of aliphatic, alkane- or alkene monocarboxylic acids as well as mixtures thereof. Sodium, potassium, magnesium, mono-, di- and tri-ethanol ammonium cations, or combinations thereof, are particularly suitable for the purposes of this invention, preferably, however, sodium or potassium soaps are used.

Particularly preferred soaps for the purpose of the present invention are the well-known alkali metal salts such as in particular the sodium and/or potassium salts of natural or synthetic aliphatic (alkanoic or alkenoic) acids having from about 8 to 22 carbon atoms, preferably from about 8 to about 20 carbon atoms, most preferably from about 10 to about 18 carbon atoms. Even more preferred are the salts of the respective saturated (alkanoic acid) acids.

It is furthermore preferred, that the soaps used in the detergent composition according to the present invention comprise at least 85% of fatty acids having from 12 to 18 carbon atoms.

Particularly preferred soaps to be used in the detergent compositions of the present invention are the sodium and/or potassium salts of stearic, palmitic, lauric and/or myristic acid.

It is well understood that the soap can be used as such, or can be formed ‘in situ’ in the detergent composition by adding the respective acid and the respective base to the composition.

The amount of the at least one soap in the detergent compositions according to the present invention is preferably selected in the range from 3 to 95 wt.-%, If the detergent composition according to the present invention is an (extruded) soap bar, the amount of the at least one soap in the detergent composition according to the present invention is preferably selected in the range from 30 to 95 wt.-% more preferably in the range from 40 to 80 wt.-%, most preferably in the range from 45 to 65 wt.-%, based on the total weight of the detergent composition.

If the composition is a liquid soap, or a cream soap, or melt and pour soap bar the amount of at least one soap in the detergent composition according to the present invention is preferably selected in the range from 3 to 35 wt.-%, more preferably in the range from 5 to 30 wt.-%, most preferably in the range from 7 to 20 wt.-%.

The detergent compositions according to the present invention may, next to the soap(s) comprise further anionic, cationic, non-ionic and/or amphoteric surfactants to form a surfactant mixture. Preferably, however, if present, the soap itself constitutes greater than 75 wt.-%, preferably greater than 80 wt.-%, more preferably greater than 85 wt.-% of the total surfactant mixture.

The water content in said liquid soap, or a cream soap, or melt and pour soap bar in all embodiments of the present invention is preferably selected in the range from 20 to 75 w.-%, most preferably in the range from 20 to 60 wt.-%, based on the total weight of said compositions.

Suitable anionic surfactants to be included into the detergent compositions according to the invention include, but are not limited to aliphatic sulphate, aliphatic sulfonate (e. g., $C_8$ to $C_{22}$ sulfonate or disulfonate), aromatic sulfonate (e. g., alkyl benzene sulfonate), alkyl sulfosuccinates, alkyl and acyl taurates, alkyl and acyl sarcosinates, sulfoacetates, alkyl phosphates, carboxylate and isethionates as well as mixtures thereof.

Particularly suitable anionic surfactants to be used for the purpose of the present invention are alkyl sulfates such as preferably sodium, triethanolamine or ammonium lauryl sulfates; alkyl ether sulfates (or Alkyl PEG-n sulfates) such as preferably sodium or ammonium lauryl ether sulfate, laureth sulfate, sodium $C_{2-15}$ pareth sulfate; alkyl amido ether sulfates; alkylaryl polyether sulfates; monoglycerides sulfates; acyl isethionate salts such as preferably sodium acylisethionate, sodium cocoyl isethionate; alkylaryl sulfonates salts such as preferably sodium alkylbenzene sulfonate and/or sodium dodecylbenzene sulfonate; alkyl sulfonates salts such as preferably sodium alkenyl sulfonate (sodium $C_{12-14}$ olefin sulfonate), sodium alkylglyceride sulfonate (sodium cocomonoglyceride olefin sulfonate), sodium alkylether sulfonate (sodium C12-15 pareth-15 sulfonate) and/or sodium lauryl sulfoacetate; (di)sodium sulfosuccinates such as preferably sodium dialkyl sulfosuccinate (dioctyl sodium sulfosuccinate), disodium alkyl PEG-n sulfosuccinate, disodium alkylamido PEG-n sulfosuccinate (disodium oleamido MEA-sulfosuccinate), disodium alkylsulfosuccinate; alkyl phosphates (mono-esters) such as preferably TEA monolauryl phosphate; PEG-n alkyl phosphates such as preferably DEA oleth-10 phosphate; di PEG-n alkyl phosphates (di-esters) such as preferably dilaureth-4 phosphate; phospholipids (tri-esters) such as preferably lecithin; carboxylic acids ester, such as preferably mono-ester of di- or tri-carboxylic acids such as lactylates (sodium acyllactylate, calcium stearoyl lactylate), laureth-6 citrate, dinonoxynol-9 citrate; ether carboxylic acids such as preferably sodium PEG-n alkyl carboxylates, sodium trideceth-13 carboxylate, nonoynol-8 carboxylic acid, alkyl $C_6$-$C_{24}$ ether carboxylates polyoxyalkylenated; acyl glutamates such as preferably di-TEA palmitoyl aspartate and sodium hydrogenated tallow glutamate; Acyl peptides with various amino acids side groups such as preferably palmitoyl hydrolysed milk protein, sodium cocoyl hydrolysed soy protein, TEA-cocoyl hydrolysed collagen or other acyl hydrolysed protein salts; sarcosinates or acyl sarcosides such as preferably myristoyl sarcosine, TEA-lauroyl sarcosinate; as well as taurates and sodium methyl acyltaurates such as preferably sodium lauroyl taurate, sodium methyl cocoyl taurate.

Particularly suitable non-ionic surfactants to be used for the purpose of the present invention encompass ethers comprising aliphatic ($C_6$-$C_{18}$) primary or secondary linear or branched chain acids, alcohols or phenols which possess no functional grouping other than the terminal OH group of the Polyoxyethylenated (POE) chain as well as ethoxylated alcohols and propoxylated POE ethers such as preferably PEG ethers, PPG ethers, propylene glycol alkyl POE-n ethers; alkyl polyglucosides of the general formula $C_nH_{2n+1}O(C_6H_{10}O_5)_xH$, with x 1 to 4 such as preferably decyl glucoside, and lauryl glucose; alkanolamides such as preferably N-acyl derivatives of monoethanolamine (MEA) and diethanolamine (DEA), ethoxylated or not; such as preferably PEG-n acylamides, coco mono- or di-ethanolamide, palmamide MEA, Acylamide DEA; esters such as preferably ethoxylated fatty acids; mono- and di-esters of fatty acids with ethylene oxide or polyethylene glycol, PEG-n acylate and diacylate such as PEG-8 laurate, PEG-8 dilaurate, PEG-150 distearate, ethoxylated glycerides such as preferably PEG-n glyceryl acylate, PEG-4 castor oil, PEG-120 glyceryl stearate, triolein PEG-6 esters, glycol esters and derivatives, mono-esters of either ethylene or propylene glycol such as preferably glycol acylate or propylene glycol acylate, monoglycerides such as glyceryl myristate or stearate, glyceryl palmitate lactate, polyglyceryl esters such as polyglyceryl-n acylate or polyglyceryl-n alkyl ether, sorbitan/sorbitol esters such as preferably acetylated sorbitan ethoxylated or not, polysorbate-n, sorbitan sequiisostearate, alkyl carbohydrates esters or sucrose esters resulting from trans-esterification of sucrose with fatty acid methyl esters or triglycerides such as preferably alkylpolysaccharides; as well as amine oxides such as preferably cocoamidopropyl amine oxide and lauramine oxide.

Particularly suitable zwitterionic and amphoteric surfactants according to the present invention encompass secondary or tertiary aliphatic amine derivatives with an aliphatic chain, linear or branched, containing at least 8 to 22 carbon atoms and one anionic group selected from the group of carboxylate, sulfonate, sulfate, phosphate or phosphonate; acyl/dialkyl ethylenediamines such as preferably acylamphoacetate, disodium acylamphodipropionate, sodium acylamphohydroxypropylsulfonate, disodium acylamphodiacetate, sodium acylamphopropionate and wherein the acyl group represents either an alkyl or alkenyl group which can be mon- or polyunsaturated and contains from 5 to 29 carbon atoms; N-alkyl amino acids or imino diacids such as preferably aminopropyl alkylglutamide, alkylaminopropionic acid, sodium alkylimino propionate, alkyl glycinates and carboxyglycinates, sodium cocoglycinates; as well as betaines such as preferably alkyl ($C_8$-$C_{20}$) betaines, alkyl amidopropyl betaines (cocamidopropyl betaines), alkyl ($C_8$-$C_{20}$) amidoalkyl (Ci-Ce) betaines, alkyl sulphobetaines and alkyl ($C_8$-$C_{20}$) amidoalkyl (Ci-Ce) sulphobetaines.

Particularly suitable cationic surfactants according to the present invention encompass alkylamines such as preferably dimethyl alkylamine (dimethyl lauramine), dihydroxyethyl alkylamine dioleate, acylamidopropyldimethylamine lactate (cocamidopropyl dimethylamine lactate); alkyl imidazolines such as preferably alkyl hydroxyethyl imidazoline, Ethylhydroxymethyl oleyl oxazoline, alkyl aminoethyl imidazoline; ethoxylated alkylamines such as preferably PEG-n alkylamines, PEG-n Alkylaminopropylamine, poloxamine; quaternary compounds such as preferably tetraalkylammonium salts; alkyl trimonium chloride, PEG-n alkylmonium chloride, dialkyldimonium chloride (hydroxyethyl cetyldimonium chloride), alkylamidopropyl alkyldimonium tosylate (Cocamidopropyl ethyldimonium ethosulfate), PEG-n Acylmethyldiethonium methosulfate, dialkyl hydroxypropylmonium methosulfate, and alkyldimonium hydroxypropyl protein hydrolysate (Cocodimonium hydroxypropyl hydrolysed hair keratin).

Preferably the surfactant is selected from the group consisting of cocoamidopropyl betaine, sodium laureth sulfate, sodium lauryl sulfate, disodium lauryl sulfosuccinate, glyceryl stearate, PEG-100 stearate as well as mixtures thereof.

Even more preferably, the detergent composition according to the present invention comprises as surfactant(s) either (a) solely soaps, i.e. at least one soap, preferably selected from the group consisting of sodium or potassium salts of stearic acid, palmitic, lauric acid and myristic acid as well as mixtures thereof (in the absence of any other surfactants) or (b) a surfactant mixture consisting of at least one soap selected from the group consisting of sodium or potassium salts of stearic acid, lauric acid, palmitic and myristic acid as well as mixtures thereof and at least one additional surfactant selected from the groups consisting of cocoamidopropyl betaine, sodium laureth sulfate, sodium lauryl sulfate disodium lauryl sulfosuccinate, glyceryl stearate, PEG-100 stearate and lauryl glucoside.

Most preferably, if a soap and an additional surfactant with all the definitions and preferences as given herein are present, then the weight-ratio of said soap(s) to said surfactant/surfactant mixture is selected in the range of 15:1 to 2:1, more preferably 10:1 to 3:1, most preferably 7.5:1 to 4:1.

The detergent compositions of the present invention may also include one or more optional ingredients such as a pearlescent or opacifying agent, a thickening agent, humectants, chelating agents, and additives which enhance their appearance, feel and fragrance, such as colorants, fragrances, preservatives, pH adjusting agents, and the like. The pH of the detergent compositions of this invention is preferably maintained in the range from about 4.5 to about 10.5, and more preferably from about 5.0 to about 10.0.

Commercially available pearlescent or opacifying agents which are capable of suspending water insoluble additives and/or which tend to indicate to consumers that the resultant product is a detergent composition are suitable for use in this invention. The pearlescent or opacifying agent may be present in an amount, based upon the total weight of the composition, of from about 1 wt.-% to about 10 wt.-%, preferably from about 1.5 wt.-% to about 7 wt.-%, and more preferably, from about 2 wt.-% to about 5 wt.-%.

Examples of suitable pearlescent or opacifying agents include, but are not limited to mono or diesters of (a) fatty acids having from about 16 to about 22 carbon atoms and (b) either ethylene or propylene glycol mono or diesters of (a) fatty acids having from about 16 to about 22 carbon atoms, (b) a polyalkylene glycol of the formula: HO-(JO)a-H, wherein J is an alkylene group having from about 2 to about 3 carbon atoms and a is 2 or 3; fatty alcohols containing from about 16 to about 22 carbon atoms; fatty esters of the formula: KCOOCH2L, wherein K and L independently contain from about 15 to about 21 carbon atoms; inorganic solids insoluble in the detergent composition, and mixtures thereof.

The pearlescent or opacifying agent may be introduced to the detergent composition as a pre-formed, stabilized aqueous dispersion, such as that commercially available from Henkel Corporation of Hoboken, New Jersey under the tradename, "Euperlan PK-3000." This material is a combination of glycol distearate (the diester of ethylene glycol and stearic acid), Laureth-4 ($CH_3(CH_2)_{10}CH_2(OCH_2CH_2)_4OH$) and cocamidopropyl betaine and preferably is in a weight percent ratio of from about 25 to about 30:about 3 to about 15:about 20 to about 25, respectively.

Commercially available thickening agents, which are capable of imparting the appropriate viscosity to the detergent compositions are suitable for use in this invention. If used, the thickener should be present in the compositions in an amount sufficient to raise the Brookfield viscosity of the composition to a value of between about 500 to about 10,000 centipoise. Examples of suitable thickening agents nonexclusively include: mono or diesters of 1) polyethylene glycol of formula: HO—(CH2CH2O)zH, wherein z is an integer from about 3 to about 200; and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. Preferred thickeners include polyethylene glycol ester, and more preferably PEG-150 distearate which is available from the Stepan Company of Northfield, Illinois or from Comiel, S.p.A. of Bologna, Italy under the tradename, "PEG 6000 DS". The amount of thickener(s) in the detergent composition is preferably selected in the range from 0 to 7 wt.-%, preferably from 1 to 5 wt.-%, most preferably from 2 to 4 wt.-%, based on the total weight of the detergent composition.

Commercially available humectants, which are capable of providing moisturization and conditioning properties to the detergent composition, are suitable for use in the present invention. Examples of suitable humectants nonexclusively include: 1) water soluble liquid polyols selected from the group comprising glycerol, propylene glycol, 1,3-propanediol, hexylene glycol, butylene glycol, dipropylene glycol, and mixtures thereof; 2) polyalkylene glycol of the formula: HO—(R"O)b-H, wherein R" is an alkylene group having from about 2 to about 3 carbon atoms and b is an integer of from about 2 to about 10; 3) polyethylene glycol ether of methyl glucose of formula $CH_3$—$C_6H_{10}O_5$—$(OCH_2CH_2)$c-OH, wherein c is an integer from about 5 to about 25; 4) urea; and 5) mixtures thereof, with glycerol being the preferred humectant.

Preferably, in all embodiments, the detergent composition comprise at least one humectant. The amount of the at least on humectant, preferably glycerol, if present in the detergent composition is preferably selected in the range from 0 to 90 wt.-%, preferably from 5 to 40 wt.-%, most preferably from 15 to 30 wt.-%, based on the total weight of the detergent composition.

Examples of suitable chelating agents include those which are capable of protecting and preserving the compositions of this invention. Preferably, the chelating agent is ethylenediamine tetraacetic acid ("EDTA"), and more preferably is tetrasodium EDTA, available commercially from Dow Chemical Company of Midland, Michigan under the tradename, "Versene 100XL" or even disodium EDTA, commercially available from BASF under tradename "EDETA BD" and is present in an amount, based upon the total weight of the composition, from about 0 to about 0.5 percent, and preferably from about 0.05 percent to about 0.25 percent.

Others suitable chelating agents include Phytic acid and its sodium salts, gluconic acid and its sodium salts and editronic acid and its sodium salts.

The amount of chelating agent(s) in the detergent composition is preferably selected in the range from 0 to 0.5 wt.-%, preferably from 0.02 to 0.3 wt.-%, most preferably from 0.05 to 0.20 wt.-%, based on the total weight of the detergent composition.

Suitable preservatives include Quaternium-15, available commercially as "Dowicil 200" from the Dow Chemical Corporation of Midland, Michigan, and are present in the composition in an amount, based upon the total weight of the composition, from about 0 to about 2.0 percent, and preferably from about 0.05 percent to about 0.10 percent.

The amount of preservative(s) in the detergent composition is preferably selected in the range from 0 to 5 wt.-%, preferably from 0.05 to 2 wt.-%, most preferably from 0.1 to 1.5 wt.-%, based on the total weight of the detergent composition.

Preferred detergent composition according to the present invention are liquid cleansing compositions, wash gels, soap bars, hair shampoos, body shampoos, hair lotions, foam baths, shower baths as well as shaving preparations.

The detergent composition of the present invention may be used on the body in conjunction with any personal cleansing implement known in the art such as a washcloth, a mesh or apertured film, pouf, sponge, brush and the like. The composition may be marketed together with one or more of such implements in a kit.

The compositions of the present invention may furthermore be "substantially free" of oils or silicones. As used herein, "substantially free" shall mean that the moisturizing cleanser composition contains, based upon the total weight of the composition, less than about 1 percent, for example, less than about 0.5 percent or less than about 0.2 percent oils and/or silicones.

In one preferred embodiment the detergent compositions according to the present invention are aqueous cleansing compositions comprising at least 20 wt.-% of water.

In another preferred embodiment, detergent compositions according to the present invention are (solid) soap bars The following examples are provided to further illustrate the compositions and effects of the present invention. These examples are illustrative only and are not intended to limit the scope of the invention in any way.

EXAMPLES

1. Foaming Properties of PENTAVITIN®

All foam tests have been done using an automated SITA foam tester R 2000.

Test Parameters:
- concentration: 5 g/l in tap water (~9.6° dH)
- sample volume: 250 ml
- sample temperature: 25° C.±1.5 K
- number of measuring series: 3
- Use of foam enhancement ring: No
- mixing conditions: 40° C. for 2 h Foam Generation:
- number of measuring intervals/stirring cycles: 60
- stirring time/measuring interval: 10 s
- stirring speed: 1500 U/min 1. Clear Solid Soap A ready to use transparent melt and pour solid soaps base was used in this example.

TABLE 1a

| Formulation clear solid soap | | | | | |
|---|---|---|---|---|---|
| Phase | Tradename | INCI Name | Ref-1 | Inv-1<br>Wt.-% | Inv-2 |
| A | Crystal SLS Free* | glycerin; aqua; sodium stearate; propylene glycol, sorbitol, sodium laurate; sodium laureth sulfate; sodium chloride; disodium lauryl sulfosuccinate; stearic acid; lauric acid; pentasodium pentetate; tetrasodium etidronate | 100 | 99.8 | 99.5 |
| B | PENTAVITIN ® | saccharide isomerate; aqua; citric acid; sodium citrate | — | 0.2 | 0.5 |

*commercial soap base (soap block)

Protocol:
- Cut the soap block into small pieces.
- Place the pieces in a beaker and heat with a water bath up to 65° C.
- Add PENTAVITIN® under slow stirring, let stir 3 min
- Slowly pour the liquid soap into the heat-resistant plastic mould.
- Once the soap has completely cooled, leave to dry for at least 24 hours.

TABLE 1b

| Foam volume after 60 stirring cycles | |
|---|---|
| | Foam volume [ml] |
| Ref-1 | 530 |
| Inv-1 | 760 |
| Inv-2 | 750 |

The samples according to present invention Inv-1 and Inv-2 containing 0.2% respectively 0.5% of PENTAVITIN® showed a significantly higher foam volume linked as well with faster foam building, highlighting the excellent foam boosting properties of the saccharide isomerate.

2. Opaque Solid Soap

A ready to use opaque melt and pour solid soap base was used in this example.

TABLE 2a

| Formulation opaque solid soap | | | | | |
|---|---|---|---|---|---|
| Phase | Tradename | INCI Name | Ref-2 | Inv-3<br>Wt.-% | Inv-4 |
| A | Crystal Goats Milk Soap* | aqua; glycerin; sodium stearate; sorbitol, sodium laurate; goat milk; propylene glycol; sodium laureth sulfate; sodium chloride; sodium lauryl sulfate; titanium dioxide; stearic acid; lauric acid; pentasodium pentetate; tetrasodium etidronate | 100 | 99.8 | 99.5 |
| A | PENTAVITIN ® | saccharide isomerate; aqua; citric acid; sodium citrate | — | 0.20 | 0.50 |

*commercial soap base (soap block)

Protocol:

- Cut the soap block into small pieces.
- Place the pieces in a beaker and heat with a water bath up to 65° C.
- Add PENTAVITIN® under slow stirring, let stir 3 min
- Slowly pour the liquid soap into the heat-resistant plastic mould.
- Once the soap has completely cooled, leave to dry for at least 24 hours.

TABLE 2b

| Foam volume after 60 stirring cycles | |
|---|---|
| | Foam volume [ml] |
| Ref-2 | 275 |
| Inv-3 | 750 |
| Inv-4 | 460 |

The samples according to present invention Inv-3 and Inv-4 containing 0.2% respectively 0.5% of PENTAVITIN® showed a higher foam volume linked as well with faster foam building. This is highlighting the foam boosting properties of the ingredient of the invention. The effect in this case is even more important with a lower concentration.

3. Cream Cleanser

A conventional cream cleanser was used in this example.

TABLE 3a

| Formulation cream cleanser | | | | |
|---|---|---|---|---|
| Phase | Ingredients | INCI Name | Ref-3<br>Wt.-% | Inv 5 |
| A | WATER DEM. | Aqua | Ad 100 | Ad 100 |
| | Edeta BD | Disodium EDTA | 0.05 | 0.05 |
| | Glycerin 99.5% | Glycerin | 25.00 | 25.00 |
| | Palmera A9914 | Myristic acid | 25.00 | 25.00 |
| | PALMAC 70-18 | Stearic acid | 5.50 | 5.50 |
| | Arlacel 165 | Glyceryl stearate, PEG-100 stearate | 3.00 | 3.00 |
| | PEG-1500 | PEG-150 | 5.00 | 5.00 |
| B | Potassium Hydroxide | Potassium hydroxide | 5.17 | 5.17 |
| C | MIRAPOL 550 SB | Polyquaternium-7 | 2.00 | 2.00 |
| | Dehyton PK 45 | Cocaamidopropyl betaine | 3.00 | 3.00 |
| | Viatenza Olive PE8 | Olive oil PEG-8 esters | 2.00 | 2.00 |
| | SERICIN | Sericin; aqua; potassium sorbate; citric acid | 0.50 | 0.50 |
| D | PENTAVITIN ® | Saccharide isomerate; aqua; citric acid; sodium citrate | 0.00 | 0.50 |

Protocol:

- Mix phase A and heat up to 70-75° C. under stirring
- Add phase B slowly (10 min) to phase A at 70-75° C. and let stir
- 100 min at 70-75° C. (200 rpm)
- Add amount of water (75° C.) which lost during heating phase
- Let cool down under stirring to 40° C.
- Add C and let stir until homogenous
- Add phase D under stirring TABLE 3b

| Foam volume after 60 stirring cycles | |
|---|---|
| | Foam volume [ml] |
| Ref-3 | 650 |
| Inv-5 | 770 |

The composition of the invention show an improvement of the foaming properties. both on the foam speed and foam volume compared to the reference.

4. In Vivo Evaluation

The following soap based cleansers (Ref-4, Inv-6) have been tested in a blind way by a group of 30 volunteers on the forearm during an in vivo study.

TABLE 4a

| Formulation soap based cleanser | | | | |
|---|---|---|---|---|
| Phase | Ingredient | INCI name | Ref-4 Wt.-% | Inv-6 Wt.-% |
| A | WATER DEM. | Aqua | Ad 100 | Ad 100 |
| | Edeta BD | Disodium EDTA | 0.05 | 0.05 |
| | Plantacare 1200 UP | Lauryl glucoside | 4.00 | 4.00 |
| | POLYGLYKOL 1500 S | PEG-32 | 5.00 | 5.00 |
| | Palmera A9912 | Lauric acid | 3.30 | 3.30 |
| | PALMERA A9818 | Stearic acid | 12.00 | 12.00 |
| | Palmera A9914 | Myristic acid | 11.50 | 11.50 |
| | Tego Care 165 | Glyceryl stearate, PEG-100 stearate | 2.00 | 2.00 |
| B | Potassium Hydroxide | Potassium hydroxide | 4.65 | 4.65 |
| | WATER DEM. | Aqua | 4.65 | 4.65 |
| C | PENTAVITIN ® | Saccharide isomerate; aqua; citric acid; sodium citrate | 0.00 | 0.50 |

Volunteers received the following guidance for the application: Moisten application area (1 forearm/product), apply product by gentle massage for 20 sec followed by 10 sec of more energetic massage and leave the foam for 1 minute. Standardized rinsing using the atomizer (3 times) and standardized drying by taping with a tissue (3 times).

Volunteers have been asked to answer two questions related to the foam properties after the first application. The results of the evaluation of the questionnaire are outlined in Table 4b.

TABLE 4b

| Results of the questionaire | | |
|---|---|---|
| | Ref-4 | Inv-6 |
| How would you describe the density of the foam? | | |
| Low | 57% | 50% |
| High | 43% | 50% |
| How would you describe the foam? | | |
| Fine and Creamy | 47% | 29% |
| Silky | 10% | 31% |
| Smooth | 23% | 31% |
| Watery | 10% | 3% |
| Sticky | 10% | 6% |
| Slippery | 0% | 0% |

The density of the foams of the formula according to the invention has been rated significantly higher than the ones of the reference formula. In addition, the foam of the formula according to the invention has been described as being more silky and smoother as well as less sticky and less watery which reflects an overall better foam texture.

2. Comparative Example with Other Sugar/Sugar Mixtures a) Prepare the Composition A and B TABLE 5a

| composition A (Shower Gel) | | | |
|---|---|---|---|
| Handelsname | INCI Name | Phase | wt.-% |
| Water Dem | AQUA | A | ad 100 |
| Texapon | SODIUM LAURETH | A | 40 |

TABLE 5a-continued

| composition A (Shower Gel) | | | |
|---|---|---|---|
| Handelsname | INCI Name | Phase | wt.-% |
| NSO - BZ | SULFATE | | |
| Tego Betain F50 | COCAMIDOPROPYL BETAINE | A | 7 |
| Antil 171 | PEG-18 GLYCERYL OLEATE/COCOATE; AQUA | B | 1.7 |
| PUROX S | SODIUM BENZOATE | C | 0.5 |
| Citric Acid Anhydrous | CITRIC ACID | C | 0.21 |
| Sodium Chloride | SODIUM CHLORIDE | C | 0.3 |

TABLE 5b

| composition B (Cream Cleanser) | | | |
|---|---|---|---|
| Handelsname | INCI Name | Phase | wt.-% |
| Water Dem | AQUA | A | ad 100 |
| Edeta BD | DISODIUM EDTA | A | 0.05 |
| Plantacare 1200 UP | LAURYL GLUCOSIDE | A | 4 |
| POLYGLYKOL 1500 S | PEG-32 | A | 5 |
| Palmera A9912 | LAURIC ACID | A | 3.3 |
| Palmera A9818 | STEARIC ACID | A | 12 |
| Palmera A9914 | MYRISTIC ACID | A | 11.5 |
| Tego Care 165 | GLYCERYL STEARATE; PEG-100 STEARATE | A | 2 |
| Potassium Hydroxide Emprove exp Ph Eur | POTASSIUM HYDROXIDE | B | 4.65 |
| Water Dem | AQUA | B | 4.65 |

b.) Prepare Solutions 1-5

TABLE 5c

| | | |
|---|---|---|
| Solution 1A: | 0.5 g | Composition A |
| | 99.5 g | Water Dem |
| Solution 1B: | 0.5 g | Composition B |
| | 99.5 g | Water Dem |
| Solution 2: | 0.1 g | PENTAVITIN ® |
| | 49.9 g | Water Dem |
| Solution 3: | 0.1 g | D-Fructose (Fluka 47739) |
| | 49.9 g | Water Dem |
| Solution 4: | 0.1 g | D-Glucose (Dextrose, Sigma D9434-250 g) |
| | 49.9 g | Water Dem |
| Solution 5: | 0.04 g | D-Fructose (Fluka 47739) |
| | 0.04 g | D-Glucose (Dextrose, Sigma D9434-250) |
| | 0.02 g | D(+) Maltose Monohydrat (Fluka 63419) |
| | 49.9 g | Water Dem |

c.) Assessment of the Foaming Properties

Put 5.0 g of Solution 1A respectively Solution 1B in a test-tube (Height 15 cm, Diameter 2.2 cm)

Add 2.5 g of solution 2/3/4/or 5 or water (Placebo)

Mark the height of liquid

Stir with VWR Analog Vortex Mixer, speed 10, Duration 1 min for mixtures comprising solution 1A Stir by hand shaking for 1 min for mixtures comprising solution 1B Mark the height of foam Measure the difference between surface of liquid (before stirring) and max height of foam (Foam height). The results are depicted in Table 5d in mm and in % based on Placebo (set to 100%).

TABLE 5d

| Results | | | | | | |
|---|---|---|---|---|---|---|
| | | Foam Height | | | | |
| # | mixture with | Solution 1A | | Solution 1B | | |
| Placebo | water | 12 mm | 100% | 22 mm | 100% | |
| Inv-7 | solution 2 (PENTAVITIN ®) | 14 mm | 117% | 28 mm | 127% | |
| Ref-5 | solution 3 (D-Fructose) | 8 mm | 67% | 20 mm | 91% | |
| Ref-6 | solution 4 (D-Glucose) | 8 mm | 57% | 20 mm | 91% | |
| Ref-6 | solution 5 (sugar mixture) | 6 mm | 50% | 25 mm | 113% | |

As can be retrieved from the results presented in table 5d, only the saccharide isomerate according to the present invention (i.e. PENTAVITIN®) leads to a significant increase in the foaming properties independent on the respective composition.

The invention claimed is:

1. A method of increasing the foaming properties of a detergent composition comprising at least one surfactant, wherein the method comprises the step of:

adding an effective amount of 0.01 to 10 wt.-%, based on the total weight of the detergent composition, of a saccharide isomerate into the detergent composition sufficient to increase the foaming properties thereof, wherein the saccharide isomerate consists essentially of the following components, based on 100 wt.-% of the saccharide isomerate:

(a) 1.5 to 5 wt.-% of psicose, (b) 1 to 5 wt.-% of mannose, (c) 10 to 30 wt.-% of fructose, (d) 20 to 60 wt.-% of glucose, and (e) 0 to 5 wt.-% of galactose.

2. The method according to claim 1, wherein the saccharide isomerate consists essentially of (a) 2 to 3 wt.-% of the psicose, (b) 1.5 to 2.5 wt.-% of the mannose, (c) 15 to 25 wt.-% of the fructose, (d) 20 to 40 wt.-% of the glucose and e) 0 to 1 wt.-% of the galactose.

3. The method according to claim 1, wherein the saccharide isomerate is present in an effective amount from 0.1 to 7.5 wt.-%, based on the total weight of the detergent composition.

4. The method according to claim 1, wherein the at least one surfactant comprises at least one soap.

5. The method according to claim 4, wherein the at least one soap is at least one selected from the group consisting of sodium or potassium salts of aliphatic acids having from 8 to 22 carbon atoms.

6. The method according to claim 4, wherein the at least one soap is selected from the group consisting of sodium or potassium salts of stearic acid, lauric acid, myristic acid and mixtures thereof.

7. The method according to claim 4, wherein the detergent composition is an extruded soap bar, and wherein the at least one soap is present in an amount from 30 to 95 wt.-%, based on the total weight of the detergent composition.

8. The method according to claim 4, wherein the detergent composition is a liquid soap, a cream soap, a melt or a pour soap bar, and wherein the at least one soap is present in an amount from 3 to 35 wt.-%, based on the total weight of the detergent composition.

9. The method according to claim 4, wherein the at least one soap constitutes greater than 75 wt.-%, based on the total weight of all surfactants present in the detergent composition.

10. The method according to claim 4, wherein the detergent composition comprises at least one additional surfactant selected from the group consisting of cocoamidopropyl betaine, sodium laureth sulfate, sodium lauryl sulfate disodium lauryl sulfosuccinate, glyceryl stearate, PEG-100 stearate, lauryl glucoside and mixtures thereof.

11. The method according to claim 1, wherein the detergent composition further comprises at least one humectant.

12. The method according to claim 11, wherein the at least one humectant is glycerol.

13. The method according to claim 1, wherein the detergent composition is a liquid cleansing composition, a wash gel, a soap bar, a hair shampoo, a body shampoo, a foam bath, a shower bath or a shaving preparation.

14. The method according to claim 1, wherein the saccharide isomerate is present in an effective amount from 0.2 to 5 wt.-%, based on the total weight of the detergent composition.

15. The method according to claim 4, wherein the at least one soap is at least one selected from the group consisting of sodium or potassium salts of aliphatic acids having from 8 to about 20 carbon atoms.

16. The method according to claim 4, wherein the at least one soap is at least one selected from the group consisting of sodium or potassium salts of aliphatic acids having from 10 to about 18 carbon atoms.

17. The method according to claim 4, wherein the detergent composition is an extruded soap bar, and wherein the at least one soap is present in an amount from 40 to 80 wt.-%, based on the total weight of the detergent composition.

18. The method according to claim 4, wherein the detergent composition is an extruded soap bar, and wherein the at least one soap is present in an amount from 45 to 65 wt.-%, based on the total weight of the detergent composition.

19. The method according to claim 4, wherein the detergent composition is a liquid soap, a cream soap, a melt or a pour soap bar, and wherein the at least one soap is present in an amount from 5 to 30 wt.-%, based on the total weight of the detergent composition.

20. The method according to claim 4, wherein the detergent composition is a liquid soap, a cream soap, a melt or a pour soap bar, and wherein the at least one soap is present in an amount from 7 to 20 wt.-%, based on the total weight of the detergent composition.

21. The method according to claim 4, wherein the at least one soap constitutes greater than 80 wt.-%, based on the total weight of all surfactants present in the detergent composition.

22. The method according to claim 4, wherein the at least one soap constitutes greater than 85 wt.-%, based on the total weight of all surfactants present in the detergent composition.

* * * * *